United States Patent
Suzuki et al.

(10) Patent No.: US 9,144,556 B2
(45) Date of Patent: Sep. 29, 2015

(54) COMPOSITION FOR PROMOTING LIPOLYSIS

(75) Inventors: Noriyuki Suzuki, Tokyo (JP); Michiaki Murakoshi, Tokyo (JP); Tomoji Ono, Tokyo (JP); Chikako Fujisaki, Tokyo (JP)

(73) Assignee: LION CORPORATION, Tokyo (JP)

( * ) Notice: Subject to any disclaimer, the term of this patent is extended or adjusted under 35 U.S.C. 154(b) by 0 days.

(21) Appl. No.: 13/979,986

(22) PCT Filed: Jan. 20, 2012

(86) PCT No.: PCT/JP2012/051186
§ 371 (c)(1),
(2), (4) Date: Jul. 16, 2013

(87) PCT Pub. No.: WO2012/099238
PCT Pub. Date: Jul. 26, 2012

(65) Prior Publication Data
US 2013/0295130 A1    Nov. 7, 2013

(30) Foreign Application Priority Data
Jan. 21, 2011 (JP) ................ 2011-011231

(51) Int. Cl.
| | |
|---|---|
| A61K 36/00 | (2006.01) |
| A61K 36/53 | (2006.01) |
| A61K 31/12 | (2006.01) |
| A23L 1/30 | (2006.01) |
| A23L 1/305 | (2006.01) |
| A61K 36/15 | (2006.01) |
| A61K 36/185 | (2006.01) |
| A61K 36/28 | (2006.01) |
| A61K 36/538 | (2006.01) |
| A61K 36/87 | (2006.01) |
| A61K 38/40 | (2006.01) |
| A61K 31/352 | (2006.01) |
| A61K 36/03 | (2006.01) |

(52) U.S. Cl.
CPC .............. *A61K 31/12* (2013.01); *A23L 1/3002* (2013.01); *A23L 1/3056* (2013.01); *A61K 31/352* (2013.01); *A61K 36/03* (2013.01); *A61K 36/15* (2013.01); *A61K 36/185* (2013.01); *A61K 36/28* (2013.01); *A61K 36/53* (2013.01); *A61K 36/538* (2013.01); *A61K 36/87* (2013.01); *A61K 38/40* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 7,235,528 | B2 * | 6/2007 | Kumagai et al. | ............. 514/4.7 |
| 7,780,873 | B2 * | 8/2010 | Mora-Gutierrez et al. | ............. 252/400.21 |
| 2004/0076690 | A1 | 4/2004 | Ikemoto et al. | |
| 2004/0234674 | A1 | 11/2004 | Eich et al. | |
| 2005/0004561 | A1 * | 1/2005 | Halas et al. | ............. 606/9 |
| 2005/0181083 | A1 | 8/2005 | Takagaki et al. | |
| 2006/0165820 | A1 * | 7/2006 | Yatcilla et al. | ............. 424/729 |
| 2007/0253941 | A1 * | 11/2007 | Naidu et al. | ............. 424/94.1 |
| 2009/0169682 | A1 | 7/2009 | Okumura et al. | |
| 2011/0182943 | A1 | 7/2011 | Kanwar et al. | |

FOREIGN PATENT DOCUMENTS

| | | |
|---|---|---|
| CN | 101156630 A * | 4/2008 |
| JP | 2003 310213 | 11/2003 |
| JP | 2004 91464 | 3/2004 |
| JP | 2004 242663 | 9/2004 |
| JP | 2004 250393 | 9/2004 |
| JP | 2004 537578 | 12/2004 |
| JP | 2005 68060 | 3/2005 |
| JP | 2006265219 A * | 10/2006 |
| JP | 2006 298911 | 11/2006 |
| JP | 2006-335758 | 12/2006 |
| JP | 2007-131620 | 5/2007 |
| JP | 2007 236222 | 9/2007 |
| JP | 2007 246541 | 9/2007 |
| JP | 2008 69121 | 3/2008 |
| JP | 2008 182934 | 8/2008 |
| JP | 2010 526873 | 8/2010 |
| KR | 10-2007-0009562 | 1/2007 |
| WO | 2010 073988 | 7/2010 |

OTHER PUBLICATIONS

Ono et al, Potent anti-obesity effect of enteric-coated lactoferrin: decrease in visceral fat accumulation in Japanese men and women with abdominal obesity after 8-week administration of enteric-coated lactoferrin Tablets. British Journal of Nutrition (2010), 104(11), 1688-1695.*

(Continued)

*Primary Examiner* — Qiuwen Mi
(74) *Attorney, Agent, or Firm* — Oblon, McClelland, Maier & Neustadt, L.L.P.

(57) ABSTRACT

It is an object of the present invention to provide a composition containing lactoferrin and another component and having a prominent effect of promoting visceral lipolysis. That is, the present invention is a composition for promoting the lipolysis; a food product, a feedstuff or a pharmaceutical product including (A) lactoferrin and (B) one or more ingredients selected from the group consisting of a *Durvillaea* extract, raspberry ketone, an artichoke leaf extract, a rosemary extract, isoflavone, a grape seed extract, a pine bark extract, a *Coleus forskohlii* extract, and a cacao extract. Also provided is a method of giving the effect of promoting the lipolysis to the food product or the feedstuff by adding the component (A) and the component (B) for promoting the lipolysis to the food product or the feedstuff.

20 Claims, No Drawings

(56) References Cited

OTHER PUBLICATIONS

Ono, T. et al., "Naizo Shibo Saibo ni Taisuru Lactoferrin no Shibao Bunkai Sokushin Sayo", Promoting action of lactoferrin on lipolysis in visceral fat cells, Journal of Japan Society for the Study of Obesity, vol. 16, No. Supplement, p. 165, (2010) (with English translation).

Murase T. et al., "Beneficial effects of tea catechins on diet-induced obesity: stimulation of lipid catabolism in the liver", International Journal of Obesity, vol. 26, pp. 1459-1464, (May 27, 2002).

Hara, Y. et al., "Suppressive Effect of Oolong Tea Polymerized Polyphenols-enriched Oolong Tea on Postprandial Serum Triglyceride Elevation", Jpn Pharmacol Ther., vol. 32, No. 6, pp. 335-343, (2004) (with English abstract).

International Search Report Issued Mar. 13, 2012 in PCT/JP12/051186 Filed Jan. 20, 2012.

Office Action issued Nov. 27, 2014, in Korean patent application No. 10 2013 7015056.

Office Action issued Aug. 4, 2015, in Korean patent application No. 10-2013-7015056.

* cited by examiner

COMPOSITION FOR PROMOTING LIPOLYSIS

TECHNICAL FIELD

The present invention relates to a composition for promoting lipolysis.

BACKGROUND

In modern life, we are chronically in a high nutrient condition, and further tend to accumulate fats in our bodies due to chronic lack of exercise. Visceral fat is a tissue that secrets bad adipocytokines that increase a risk for hypertension, hyperglycemia, hyperlipidemia, and the like. Thus, materials having a function that reduces the visceral fat effortlessly have been being developed. Catechins that exert their effect by being ingested with exercise (Nonpatent Literature 1) and polyphenols that suppress absorption of fat (Nonpatent Literature 2) are reported to be available as such materials.

Patent Document 1 describes that combination of lactoferrin with a blood circulation accelerator exerts an effect of reducing the visceral fat by suppressing the accumulation of fat.

RELATED ART DOCUMENTS

Patent Literature

Patent Literature 1: Japanese Patent Application Laid-open No. 2008-69121-A

Nonpatent Literature

Nonpatent Literature 1: International Journal of Obesity, 26: 1459-1464, 2002.
Nonpatent Literature 2: Japanese Pharmacology and Therapeutics, 32(6): 335-342, 2004.

SUMMARY OF THE INVENTION

Problem to be Solved by the Invention

However, the effect of reducing the visceral fat by the conventional combination of lactoferrin with the blood circulation accelerator could not be said to be sufficient.

It is an object to provide a composition containing lactoferrin and another component and having a prominent effect of promoting visceral lipolysis.

Means for Solving Problem

The present invention provides the following inventions:
[1] A composition for promoting lipolysis comprising:
(A) lactoferrin; and
(B) one or more ingredients selected from the group consisting of a *Durvillaea* extract, raspberry ketone, an artichoke leaf extract, a rosemary extract, isoflavone, a grape seed extract, a pine bark extract, a *Coleus forskohlii* extract, and a cacao extract.
[2] The composition for promoting the lipolysis according to claim 1, which is a food product, a feedstuff, or a pharmaceutical product.
[3] A method of giving an effect of promoting lipolysis to a food product or a feedstuff by adding
(A) lactoferrin; and
(B) one or more ingredients selected from the group consisting of a *Durvillaea* extract, raspberry ketone, an artichoke leaf extract, a rosemary extract, isoflavone, a grape seed extract, a pine bark extract, a *Coleus forskohlii* extract, and a cacao extract to the food product or the feedstuff.

The present invention may include the following aspects:
[4] A method for promoting lipolysis of a subject wherein a composition for promoting lipolysis comprising the following (A) and (B) is administered to the subject:
(A) lactoferrin; and
(B) one or more ingredients selected from the group consisting of a *Durvillaea* extract, raspberry ketone, an artichoke leaf extract, a rosemary extract, isoflavone, a grape seed extract, a pine bark extract, a *Coleus forskohlii* extract, and a cacao extract.
[5] The method for promoting the lipolysis according to [4], wherein the composition for promoting lipolysis is administered orally.
[6] The method for promoting the lipolysis according to [5], wherein the composition for promoting lipolysis is a food product, a feedstuff, or a pharmaceutical product.

Effect of the Invention

The composition for promoting lipolysis of the present invention exerts a synergistic effect of the component (A) and the component (B) to have the action for promoting the lipolysis, which is unexpectedly more prominent than the action obtained from each component alone.

EMBODIMENTS FOR CARRYING OUT THE INVENTION

The composition for promoting lipolysis of the present invention contains the following component (A) and component (B):
(A) lactoferrin, and
(B) one or more ingredients selected from the group consisting of raspberry ketone, an artichoke leaf extract, a cacao extract, a grape seed extract, a pine bark extract, a *Coleus forskohlii* extract, a *Durvillaea* extract, a rosemary extract, and isoflavone.

The component (A) is lactoferrin. Examples of lactoferrin are as follows: commercially available lactoferrin; lactoferrin separated from colostrum, transitional milk, normal milk or late lactation milk from mammalian animals such as human, bovine, ovine, goat, horse, or defatted milk or whey that is a product obtained by processing these milks using a standard method such as ion exchange chromatography; lactoferrin produced from a plant (tomato, rice, tobacco); and lactoferrin obtained by genetic modification. Commercially available lactoferrin may be used or those prepared using a known method may be used.

Lactoferrin may be used alone or in appropriate combination of two or more. Bovine lactoferrin is preferred as lactoferrin.

An amount of the component (A) to be combined in the composition of the present invention is generally 5 mg to 5,000 mg/day, preferably 50 mg to 1,000 mg/day, and more preferably 100 mg to 500 mg/day as an intake per day for human. This range gives the composition for promoting the lipolysis that is prominently excellent in effect of promoting the lipolysis. There is also no problem in terms of cost and safety of the composition.

The component (B) is composed of one or more ingredients selected from the group consisting of a *Durvillaea* extract, raspberry ketone, an artichoke leaf extract, a rosemary extract, isoflavone, a grape seed extract, a pine bark extract, a *Coleus forskohlii* extract, and a cacao extract.

(B-1) *Durvillaea* Extract

The *Durvillaea* extract is an extract from *Durvillaea*. *Durvillaea* is a seaweed belonging to family Durvilleaceae, genus *Durvillaea*, and *Durvillaea antarctica, Durvillaea potatorum, Durvillaea willana*, and the like are called bull kelps. The *Durvillaea* extract may be obtained by extracting either from a whole plant body or a part thereof of *Durvillaea*. A condition for preparing the extract is not particularly limited. A solvent containing alcohol is preferable, a solvent in which a ratio of alcohol to water is 0/100 to 70/30 (volume ratio, v/v) is more preferable, and a solvent in which a ratio of alcohol to water is 0/100 to 40/60 is still more preferable. An extraction temperature is not particularly limited, and is generally 5 to 80° C. and preferably 5 to 50° C. An extraction time period is generally 1 to 24 hours. It is preferable to extract with stirring. A pH value for the extraction is not particularly limited unless it goes to an extreme acidic or alkaline pH.

(B-2) Raspberry Ketone

Raspberry ketone is 4-(4-hydroxyphenyl)-2-butanone and/or p-hydroxybenzylacetone. Raspberry ketone is one of perfume ingredients of raspberry. Raspberry ketone may be derived from a natural product such as a plant body (e.g., low tree, fruit) of a plant belonging to *Rosaceae Rubus* such as raspberry or may be an artificial product by chemical synthesis and the like.

Examples of raspberry ketone derived from the natural product may include an extract from the plant body of the plant belonging to Rosaceae *Rubus* (hereinafter referred to as a raspberry extract). The plant belonging to Rosaceae *Rubus* may preferably include raspberry. Raspberry (English name; framboise in French) has a scientific name of *Rubus idaeus* L., *Rubus strigosus* and corresponds to subgenus *Idaeobatus* taxonomically. A portion to be extracted in the plant body when the raspberry extract is obtained may be either a whole plant body or a part thereof, and is preferably a low tree or a fruit. A preparation condition such as an extraction solvent and an extraction temperature is not particularly limited. A purity of the raspberry extract is not particularly limited as long as the extract contains raspberry ketone.

(B-3) Artichoke Leaf Extract

The artichoke leaf extract is an extract from a leaf of artichoke (scientific name: *Cynara scolymus* L. (Compositae)). The artichoke leaf extract may be extracted from a part of the leaf or the whole leaf. The condition for preparing the extract is not particularly limited. Alcohol is preferable and ethanol is more preferable as the solvent.

Cynaropicrin (2-(hydroxymethyl) propenoic acid [(3aR, 6aβ, 9aβ, 9bα)-dodecahydro-8α-hydroxy-3,6,9-trismethylene-2-oxoazuleno[4,5-b]furan-4β-yl) is contained in the artichoke leaf extract, and its content is generally about 0.7% by mass.

(B-4) Rosemary Extract

The rosemary extract is an extract from rosemary. Rosemary also has a Japanese name of man-nenrow and a scientific name of *Rosmarinus officinalis* L., and is an evergreen low tree belonging to Lamiaceae. The rosemary extract may be obtained by extracting the whole plant body or a part thereof of rosemary. The condition for preparing the extract is not particularly limited. Water, alcohol, or a combination thereof is preferable and the combination of water with ethanol is more preferable as the solvent.

(B-5) Isoflavone

Isoflavone is 3-phenylchromone (3-phenyl-4H-1-benzopyran-4-one). Isoflavone is preferably aglycone (isoflavone aglycone) obtained by removing sugars from a glycoside form. Isoflavone may be derived from a natural product or may be an artificial product by chemical synthesis and the like.

Examples of isoflavone derived from the natural product may include soybean extracts, and of these, an extract of fermented soybean (hereinafter referred to as a fermented soybean extract) is preferred. The fermented soybean is obtained by fermenting the soybean with a microorganism. The fermentation can be progressed by adding the microorganism such as *aspergillus* to the soybean, which is then placed under an optimal condition. The condition for preparing the extract from the fermented soybean is not particularly limited, and examples of the solvent may include alcohol. The extract from the fermented soybean generally contains isoflavone in an amount of 30 to 40% by mass.

(B-6) Grape Seed Extract

The grape seed extract is an extract of a seed from a grape (long trailing low tree of Vitaceae). The seed is targeted to be extracted. The condition for preparing the grape seed extract is not particularly limited, and water and alcohol are preferred as the solvent. When the water is used as the solvent, it is preferable to extract from the grape seed with the water at 70° C. or above (preferably 80 to 120° C., and more preferably 80 to 100° C.) Proanthocyanidine is contained in the grape seed extract, and its content is generally about 38% by mass.

(B-7) Pine Bark Extract

The pine bark extract is an extract from a bark of a pine (plant belonging to genus *Pinus*). *Pinus radiata* is exemplified as the pine. The condition for preparing the extract is not particularly limited, and water is preferred as the solvent. Proanthocyanidine, catechin, flavonoid, and the like are contained in the pine bark extract.

(B-8) *Coleus forskohlii* Extract

The *Coleus forskohlii* extract is an extract from a plant body of *Coleus forskohlii*. *Coleus forskohlii* is a perennial belonging to genus *Coleus*, family Lamiaceae, and its scientific name is *Coleus forskohlii, Coleus barbatus*, or *Plectranthus barbatus*. The *Coleus forskohlii* extract may be extracted from either a whole or a part of the plant body of *Coleus forskohlii*. The condition for preparing the extract is not particularly limited, and forskolin that is one of diterpene is contained in the *Coleus forskohlii* extract.

(B-9) Cacao Extract

The cacao extract is an extract from Sterculiaceae, cacao (scientific name: *Theobroma cacao*). The cacao extract may be extracted from either a whole or a part of the plant body of cacao. A portion to be extracted may include a cacao pod and a cacao seed. The seed is preferable and a cacao husk is more preferable. The cacao husk means a coat around a cacao bean (seed) surrounded with white fruit pulp in a cacao pod. The condition for preparing the cacao extract is not particularly limited. Alcohol is preferable as the solvent, and aqueous ethanol (e.g., aqueous ethanol containing ethanol at 50 to 80% by volume) is more preferable.

Theobromine (3,7-dimethylxanthine) is contained in the cacao extract, and its content is generally 10% by mass. Polyphenol is also contained in the cacao extract, and its content is generally about 20% by mass. Further, phenylethylamine (2-phenylethylamine) and γ-aminobutyric acid are also contained in the cacao extract.

The component (B) may be one or more selected from the group consisting of the *Durvillaea* extract, raspberry ketone, the artichoke leaf extract, the rosemary extract, isoflavone, the grape seed extract, the pine bark extract, the *Coleus forskohlii* extract, and the cacao extract, or may be a combination of two or more selected therefrom. When two or more are combined, the combination containing one or two or more selected from the *Coleus forskohlii* extract, the *Durvillaea* extract, and the rosemary extract is preferable. The more preferable combinations are as follows: the combination of the *Coleus forskohlii* extract and the *Durvillaea* extract; the combination of the *Coleus forskohlii* extract and the rosemary extract; the combination of the *Durvillaea* extract and the rosemary extract; and the combination of the *Coleus forskohlii* extract, the *Durvillaea* extract, and the rosemary extract.

An amount of the component (B) to be combined is generally 0.01 mg to 50 g/day, preferably 0.1 mg to 10 g/day, and more preferably 1 mg to 1,000 mg/day as an intake per day for human. This range gives the composition for promoting the lipolysis that is prominently excellent in effect of promoting the lipolysis. This range also has no problem in terms of cost and safety of the composition. When two or more ingredients are used as the component (B), a total amount of two or more to be combined is the above amount of the component (B) to be combined.

A ratio of the component (A) to the component (B) to be combined is generally 10:1 to 1:10, preferably 5:1 to 1:5 and more preferably 3:1 to 1:3 as the intake per day for human. This range gives the composition for promoting the lipolysis that is prominently excellent in effect of promoting the lipolysis.

The composition for promoting the lipolysis promotes breakdown of fat. Promoting the breakdown of the fat in the present invention means that a degree such as speed or amount of the breakdown of the fat in the body is increased than usual.

Promoting the breakdown of the fat by the composition for promoting the lipolysis of the present invention can be confirmed, for example, by conducting Examples. That is, a sample is added to a precursor adipocyte prepared from rat mesenteric tissue, and glycerol is quantified. A commercially available kit such as F-Kit Glycerol (supplied from Roche, product number: 14820) may be used for the quantification. When the amount of obtained glycerol is larger than the amount of glycerol when the sample was not added, it can be confirmed that the lipolysis was promoted.

A subject that the composition for promoting the lipolysis of the present invention targets is not particularly limited. This composition is useful for human and vertebrates other than the human. A healthy condition of the human or the vertebrate other than the human that is the subject does not matter. This composition is suitable for, for example, subjects who feel to be overweight, subjects who want to lose weight, and subjects who want to prevent a lifestyle related disease such as hypertension, hyperglycemia and hyperlipidemia. Even a subject having no particular problem can routinely digest this composition for the purpose of promoting the lipolysis.

The composition for promoting the lipolysis of the present invention may combine a pharmaceutically acceptable carrier in addition to the above components (A) and (B) as the active components. Examples of the pharmaceutically acceptable carrier may include oil ingredients, lubricants, diluents, binders, disintegrants, and coating agents. Additives such as sweeteners, acidic flavoring agents, flavoring agents, coloring agents, food colors, color former, taste-masking agents, antioxidants, preservatives, tasting agents, nutrient supplement, vitamin agents, leavening agents, thickeners, and surfactants may be contained appropriately in appropriate amounts.

Examples of the oil ingredients may include various fatty acid esters, hydrocarbons, higher fatty acids, higher alcohols, and the like. Examples of the lubricants may include magnesium stearate, stearic acid, sodium stearyl fumarate, sucrose fatty acid ester, polyethylene glycol (macrogol), talc.

Examples of the binders may include hydroxypropylcellulose, hydroxypropylmethylcellulose, methylcellulose, gelatin, starch, dextrin, gum arabic, sodium alginate, tragacanth, purified gelatin, polyvinyl alcohol, polyvinyl pyrrolidone, methylcellulose, polyvinyl alcohol (partially saponified), ethylcellulose, pullulan, polyethylene glycol (macrogol), and the like.

Examples of the disintegrants may include calcium carboxymethylcellulose (carmellose calcium), sodium carboxymethylcellulose (carmellose sodium), low substitution degree hydroxypropylcellulose, carboxymethylcellulose, sodium carboxymethylstarch, crosslinked sodium carboxymethylcellulose (cross-carmellose sodium), powdered cellulose, cellulose or derivatives thereof, crosslinked polyvinyl pyrrolidone (cross-povidone), starch, carboxymethylstarch, hydroxypropylstarch, agar, and the like.

Examples of the diluents may include the following compounds: polysaccharides such as crystalline cellulose, sodium alginate, and xanthan gum; starch and derivatives thereof such as pregelatinized starch, hydroxypropylstarch, corn starch, and potato starch; sugars and sugar alcohols such as sucrose, glucose, xylitol, erythritol, sorbitol, lactitol, trehalose, palatinose, palatinit (reduced palatinose), mannitol, maltitol, lactitol, lactose, fructose, and powdered reduced malt syrup; cellulose and derivatives thereof such as powdered cellulose, partially pregelatinized starch, and ethylcellulose; and light silicic anhydride, titanium oxide, aluminium hydroxide gel, synthesized aluminium silicate, aluminium trisilicate, silicon dioxide, kaolin, cacao butter, citric acid or salts thereof, stearic acid or salts thereof, calcium hydrogen phosphate, and sodium hydrogen phosphate.

Examples of the sweeteners may include aspartame, acesulfame potassium, saccharin sodium, sucralose, stevia, thaumatin, and the like. Examples of the acidic flavoring agents may include Citric acid, succinic acid, tartaric acid, malic acid, fumaric acid, and the like. Examples of the flavoring agents may include various perfumes such as monoterpenes such as menthol, camphor, borneol, limonene, various flavors, and the like.

A dosing form of the composition for promoting the lipolysis of the present invention is not particularly limited. Examples of the dosing form may include oral administration such as buccal administration, sublingual administration and parenteral administration such as intravenous administration, intramuscular administration, subcutaneous administration, transdermal administration, transnasal administration, transpulmonary administration. Of these, a less invasive dosing form is preferable, and the oral administration is more preferable.

A dosage form of the composition for promoting the lipolysis of the present invention is not particularly limited, and can be selected appropriately depending on the dosing form. Examples of the dosage form when administered orally may include a liquid (liquid agent), a syrup form (syrup agent), a tablet form (tablet), a capsule form (capsule agent), a powdered form (granule, fine granule), a soft capsule form (soft capsule agent), a liquid (liquid agent), a syrup form (syrup agent), a solid form, a semi-liquid form, a cream form, and a paste form.

A method for producing the composition for promoting the lipolysis is not particularly limited and can be appropriately selected depending on the dosage form. For example when the dosage form is a tablet, a method in which lactoferrin and optional ingredients to be combined as needed are mixed and then the resulting mixture is compressed and molded to obtain the tablet and a method in which the tablet obtained after being compressed and molded as above is further coated with an ingredient being capable to dissolve in intestines (to make an enteric-coated tablet) are included, and the latter is more preferable. The ingredient being capable to dissolve in intestines may include shellac, hydroxymethylcellulose phthalate, carboxymethylcellulose, aminoalkyl methacrylate copolymers, beer yeast cell walls such as brand name, Yeast-Wrap, etc., tapioca starch, gelatin, and pectin, and of these, shellac is preferable. It can be confirmed by a disintegration test in Japanese Pharmacopoeia 14th revision whether the substance is the enteric-coated tablet or not.

The composition for promoting the lipolysis of the present invention exhibits a promotion effect that is excellent in breakdown of the fat. Thus, this is effective for prevention and treatment of obesity. According to the composition for promoting the lipolysis of the present invention, it is anticipated to reduce the visceral fat. Thus, it is anticipated to efficiently prevent and treat the lifestyle related disease such as hypertension, hyperglycemia, hyperlipidemia, and the like.

A method for oral administration can be determined appropriately depending on conditions such as concentrations of the components (A) and (B) to be combined, the dosage form, an age, bodyweight and sex of the subject to be administered, and an exercise load when a dose is received before an exercise. For example when the dosage form is the tablet, it is preferable to take the tablet together with water and the like. A dosing interval can be determined appropriately, and the dose may be received before, after, or during a meal.

The administration of one or two or more other agents or compositions for promoting the lipolysis may be combined in addition to the administration of the composition for promoting the lipolysis of the present invention. Alternatively, a composition including one or two or more other ingredients having the effect of promoting the lipolysis in addition to the combination of the components (A) and (B) may be made as the composition for promoting the lipolysis of the present invention.

The lipolysis can be promoted by giving the composition for promoting the lipolysis to the human or the vertebrate other than the human. Thus, the composition for promoting the lipolysis of the present invention is useful as a pharmaceutical, a quasi-drug, a food product, and a feedstuff.

The food product is generally a processed food product, and examples thereof may include beverages such as soft drinks, carbonated drinks, energy drinks, powdered drinks, fruit drinks, milk drinks, and jelly drinks, confectioneries such as cookies, cakes, chewing gums, candies, tablets, gummies, "manju" (steamed yeast buns with filling), "Yokan" (adzuki bean jellies), puddings, jellies, ice creams, and sherbet, marine processed products such as "Kamaboko" (boiled fish pastes), "chikuwa" (tubular rolls of boiled fish paste), and "happen" (puffy cakes made of ground fish), livestock processed products such as hamburgers, hams, sausages, wiener sausages, cheeses, butters, yogurt, fresh creams, cheeses, margarines, and fermented milk, soups such as powdered soups, and liquid soups, staple foods such as rice, noodles (dried noodles, fresh noodles), breads, and cereals, and seasonings such as mayonnaise, shortening, dressing, sauce, "tare" (Japanese sauce), and soy sauce. Further, the composition for promoting the lipolysis of the present invention may be a healthy food, a functional food, a food with health claims, a food for specified health use, a food with nutrient function claims, a nutritional supplement (supplement), a food for medicine, a food for the sick, a food for the infant, a food for the care, a food for the elderly, and the like.

An ingestion time of the food product including the composition for promoting the lipolysis is not particularly limited here. For example, the food product may be ingested before or after the meal and before or after the exercise.

When the composition for promoting the lipolysis is used as the food product, it is preferable to display the effect of the present invention. Examples of the display for the effect of the present invention may include the display that the food product is used for promoting the breakdown of the fat.

The breakdown of the visceral fat is promoted by administering the composition for promoting the lipolysis of the present invention as the food products to the human as described above. Therefore, the composition for promoting the lipolysis of the present invention is useful as various food products for obesity prevention, weight loss, and prevention of the lifestyle related diseases.

The composition for promoting the lipolysis of the present invention is also useful as the feedstuff because even when this is administered to the vertebrate such as a pet animal other than the human, the effect of promoting the breakdown of the visceral fat can also be anticipated.

Further, the components (A) and (B) in the composition for promoting the lipolysis of the present invention can be added to an ordinary food product or feedstuff to give the effect of promoting the lipolysis to that food product or feedstuff.

EXAMPLES

The present invention will be described in detail below based on Examples. The present invention is not limited to these Examples.

Experimental Examples 1 to 9 and Comparative Experimental Examples 1 to 4

Preparation of Rat Mesenteric Adipocytes

Two SD rats (male, 10 weeks of age, Japan SLC, Inc.) were used. The rats were euthanized under anesthesia with ether and anatomized, and mesenteric adipose tissue was removed. The obtained tissue was placed in a sterilized petri dish, immersed in ice-cold saline (Otsuka Normal Saline, supplied from Otsuka Pharmaceutical Co., Ltd.) containing 1% antibiotic (Antibiotic-Antimycotic Stabilized, supplied from Sigma, A5955), and washed to remove blood and hairs, particularly lymphocytes (washed several times with different saline until no hair was visible). The tissue was cut using ophthalmic scissors (cut 25 times per 1 g of the tissue), and dispersed by stirring every several minutes in a PBS solution containing 1 mg/mL of collagenase (Collagenase S-1 derived from *Actinomycetes*, supplied from Nitta Gelatin Inc.) at 37° C. for 40 minutes. Roughly, the tissue from one rat was treated with 20 mL of the collagenase solution.

The tissue suspension was filtrated through a cell strainer with a pore size of 100 µm (REF352360 supplied from BD Falcon). Subsequently, a viscosity of the suspension was reduced by adding 20 mL of DMEM (Dulbecco's Modified Eagle's Medium-high glucose, D5796 supplied from Sigma), and then the suspension was centrifuged at 800 rpm for 10 minutes. An oil layer in an upper layer was removed using an aspirator, and then, the resulting suspension was resuspended and filtrated through a cell strainer with a pore size of 70 µm (REF352350 supplied from BD Falcon). After centrifuging at 800 rpm for 15 minutes, it was confirmed that there was no suspended cell in a supernatant, the presence of a pellet was confirmed, and then the supernatant was removed. The pellet was suspended in 5 mL of DMEM (serum free), the suspension was centrifuged at 800 rpm for 15 minutes, and then the supernatant was removed.

The resulting pellet was gently suspended in 5 mL of a medium for visceral adipocyte differentiation (Visceral Adipocyte Culture Medium, 250 mL, code: VACMR supplied from Primary Cell Co., Ltd.). The suspension was diluted to 10 times, and the number of cells was counted and was $1.015 \times 10^7$ cells/mL. $2.54 \times 10^7$ cells could be recovered from one rat. The cells suspended in the medium were placed so as to be at $6 \times 10^6$ cells/24-wells and 500 μL/well, and their cultivation was started. On the following day, 500 μL of the medium was added, and subsequently the medium was changed every third day. Thereafter, the medium was changed every third day. On the 6th day after the start of the cultivation, the medium was changed to a medium containing each sample. A culture supernatant was collected 48 hours after adding the sample, and the cultivation was terminated. It was visually confirmed that there was no cytotoxicity in all of the cultivations.

Preparation of Sample

Samples used in each Example and Comparative Example were prepared. Lactoferrin (supplied from DMV), raspberry ketone (supplied from Takasago International Corporation), an artichoke leaf extract (brand name: Biobenefity F supplied from Ichimaru Pharcos Co., Ltd.), a cacao extract (Cacao extract-P supplied from Oryza Oil & Fat Chemical Co., Ltd.), a grape seed extract (brand name: Gravinol supplied from Kikkoman Corporation), a pine bark extract (Enzogenol supplied from Enzo Nutraceuticals Limited), a *Coleus forskohlii* extract (supplied from Natural Remedies Pvt. Ltd.), a *Durvillaea* extract, a rosemary extract (brand name: Leomeal supplied from Lion Corporation), soybean isoflavone aglycone (supplied from Kikkoman Corporation), a ginger extract (supplied from Nippon Funmatsu Yakuhin Co., Ltd.), epigallocatechin gallate (supplied from Wako Pure Chemical Industries Ltd.), and chlorogenic acid (supplied from Wako Pure Chemical Industries Ltd.) were used as ingredients in the samples. Biobenefity F used as the artichoke leaf extract contains dextrin in an amount of 70% by mass as the diluent, but an amount of the combined artichoke leaf extract in Table 1 is a value in terms of removing the diluent.

The *Durvillaea* extract was extracted under the following condition. The *Durvillaea* extract was obtained by stirring 10 g of dried *Durvillaea* in aqueous ethanol (alcohol/water=30/70 (v/v)) in 20 times its weight for 3 hours and then distilling off its supernatant.

A concentration of lactoferrin was adjusted to 30 ppm or 10 ppm, and lactoferrin at each concentration was used as the sample for evaluating the effect of lactoferrin alone (Comparative Experimental example 1). Each ingredient other than lactoferrin was used as the sample for evaluating the effect of a single preparation alone as follows. Lactoferrin and each ingredient other than lactoferrin were adjusted to the following concentrations and mixed to use as the sample for evaluating the effect of a combined preparation (Experimental Examples 1 to 9 and Comparative Experimental Examples 2 to 4).

(Samples for Evaluating Single Preparation)
Each ingredient other than lactoferrin: 30 ppm
Each ingredient other than lactoferrin: 10 ppm
(Samples for Evaluating Combined Preparation (+Lactoferrin 30 ppm))
Each ingredient other than lactoferrin: 30 ppm+lactoferrin 30 ppm
Each ingredient other than lactoferrin: 10 ppm+lactoferrin 30 ppm
(Samples for Evaluating Combined Preparation (+Lactoferrin 10 ppm))
Each ingredient other than lactoferrin: 30 ppm+lactoferrin 10 ppm
Each ingredient other than lactoferrin: 10 ppm+lactoferrin 10 ppm Quantification of Glycerol Concentration Glycerol was quantified using F-Kit Glycerol (product No. 14820 supplied from Roche). Absorbance was measured using Novaspec Plus (supplied from Amersham Bioscience). 1.0 mL of a solution I dissolved in 11 mL of distilled water, 2.0 mL of distilled water, 0.1 mL of each sample described above, and 0.01 mL of a solution II were added. The mixture was mixed well, and reacted at room temperature for 5 minutes. The absorbance at AB 340 nm (E1) was measured. 0.01 mL of a solution III was added thereto. The mixture was mixed well and reacted at room temperature for 7 minutes. Then, the absorbance (E2) was measured. Standard solutions included in the kit were used as controls.

The concentration of glycerol was calculated based on the measured absorbance values by the following calculation formula I according to attached instructions.

$$\text{Glycerol (g/L)} = V \times MW / \epsilon \times d \times v \times 1000 \times \delta E \times \text{dilution} \quad \text{(Calculation formula I)}$$

$\delta E = (E2-E1)\text{sample} - (E2-E1)\text{blank}$
V (amount of reaction solution): 3.02 mL
MW (molecular weight): 92.1
d (optical path length): 1 cm
$\epsilon$ (absorbance coefficient): 6.3 ($1 \times \text{mmol}^{-1} \times \text{cm}^{-1}$)
v (amount of specimen): 0.1 mL
(Calculation of Glycerol Concentration Based on Calculation Formula I)

$$\text{Glycerol (g/L)} = 3.02 \times 92.1/6.3 \times 1 \times 0.1 \times 1000 \times \delta E = 0.441 \times \delta E \times \text{dilution rate}$$

A relative amount of glycerol in each of Experimental Examples and Comparative Experimental Examples was calculated when an amount of glycerol in an additive free group was 0%, and the relative amount was described as a rate of promoting the lipolysis. The rate of promoting the lipolysis in each of Experimental Examples and Comparative Experimental Examples is shown in Table 1-1 (evaluation of single preparations), Table 1-2 (evaluation of combined preparations (combined with lactoferrin 30 ppm)), and Table 1-3 (evaluation of combined preparations (combined with lactoferrin 10 ppm)).

Results

As shown in Table 1, the rates of promoting the lipolysis in the evaluation of the combined preparations in Experimental Examples 1 to 9 exceeded the values obtained by adding the rates of promoting the lipolysis in the evaluation of the single preparations at corresponding concentration.

To cite a case, the rate of promoting the lipolysis 32% in Experimental Example 9 in the combined preparation (isoflavone 10 ppm+lactoferrin 10 ppm in Table 1-3) exceeded a value obtained by adding the rate of promoting the lipolysis 12.1% (Table 1-1) obtained from lactoferrin 10 ppm alone in Comparative Experimental Example 1 in the single preparation and the rate of promoting the lipolysis 0% obtained from isoflavone alone in Experimental Example 9 in the single preparation. To cite another case, raspberry ketone (Experimental Example 1) alone and the pine bark extract (Experimental example 5) alone rather inhibited the lipolysis at 10 ppm in the single preparation (Table 1-1), but each of them in combination with lactoferrin 10 ppm exhibited unexpectedly the more excellent effect of promoting the lipolysis than in the case of lactoferrin 10 ppm alone (Table 1-3).

On the other hand, the rate of promoting the lipolysis in Comparative Experimental Example 2 in each combined preparation was below a value obtained by adding the rate of promoting the lipolysis in Comparative Experimental Example 2 in the single preparation and the rate of promoting the lipolysis in Comparative Experimental Example 1 in the single preparation. No prominently synergistic effect as seen in Experimental Examples 1 to 9 was observed also in Comparative Experimental Examples 3 and 4.

These results indicate that the synergistic effect is exerted and the unexpectedly prominent effect of promoting the lipolysis is exerted by combining the component (A) and the component (B) in the present invention.

TABLE 1-1

Rate of promoting lipolysis (single preparation)

| | | Concentration of each ingredient | |
|---|---|---|---|
| | | 30 ppm | 10 ppm |
| Comparative Experimental Example 1 | Lactoferrin | 21.3 | 12.1 |
| Experimental Example 1 | Raspberry ketone | 10 | −2 |
| Experimental Example 2 | Artichoke leaf extract | 10 | 21 |
| Experimental Example 3 | Cacao extract | 23 | 15 |
| Experimental Example 4 | Grape seed extract | 50 | 53 |
| Experimental Example 5 | Pine bark extract (*Pinus radiata*) | 1 | −5 |
| Experimental Example 6 | *Coleus forskohlii* extract | 76 | 37 |
| Experimental Example 7 | *Durvillaea* extract | 8 | 2 |
| Experimental Example 8 | Rosemary extract | 45 | 18 |
| Experimental Example 9 | Isoflavone aglycone | 1 | 0 |
| Comparative Experimental Example 2 | Ginger extract | 2 | 3 |
| Comparative Experimental Example 3 | Epigallocatechin gallate | 3 | −6 |
| Comparative Experimental Example 4 | Chlorogenic acid | 5 | 3 |

TABLE 1-2

Rate of promoting lipolysis (combined preparation (+ lactoferrin 30 ppm))

| | | Concentration of each ingredient | |
|---|---|---|---|
| | | 30 ppm | 10 ppm |
| Experimental Example 1 | Raspberry ketone | 70 | 57 |
| Experimental Example 2 | Artichoke leaf extract | 64 | 73 |
| Experimental Example 3 | Cacao extract | 77 | 69 |
| Experimental Example 4 | Grape seed extract | 106 | 112 |
| Experimental Example 5 | Pine bark extract (*Pinus radiata*) | 55 | 54 |
| Experimental Example 6 | *Coleus forskohlii* extract | 156 | 100 |
| Experimental Example 7 | *Durvillaea* extract | 83 | 81 |
| Experimental Example 8 | Rosemary extract | 119 | 93 |
| Experimental Example 9 | Isoflavone aglycone | 62 | 57 |
| Comparative Experimental Example 2 | Ginger extract | 23 | 22 |
| Comparative Experimental Example 3 | Epigallocatechin gallate | 24 | 21 |
| Comparative Experimental Example 4 | Chlorogenic acid | 22 | 20 |

TABLE 1-3

Rate of promoting lipolysis (combined preparation (+ lactoferrin 10 ppm))

| | | Concentration of each ingredient | |
|---|---|---|---|
| | | 30 ppm | 10 ppm |
| Experimental Example 1 | Raspberry ketone | 34 | 22 |
| Experimental Example 2 | Artichoke leaf extract | 61 | 42 |
| Experimental Example 3 | Cacao extract | 45 | 38 |
| Experimental Example 4 | Grape seed extract | 90 | 85 |
| Experimental Example 5 | Pine bark extract (*Pinus radiata*) | 33 | 26 |
| Experimental Example 6 | *Coleus forskohlii* extract | 116 | 82 |
| Experimental Example 7 | *Durvillaea* extract | 38 | 22 |
| Experimental Example 8 | Rosemary extract | 79 | 57 |
| Experimental Example 9 | Isoflavone aglycone | 36 | 32 |
| Comparative Experimental Example 2 | Ginger extract | 13 | 13 |
| Comparative Experimental Example 3 | Epigallocatechin gallate | 13 | 11 |
| Comparative Experimental Example 4 | Chlorogenic acid | 14 | 12 |

Experimental Examples 10 to 13 and Comparative Experimental Examples 5 to 7

The rate of promoting the lipolysis was evaluated in the same manner as in Experimental Example 1, except that combinations shown in Table 2 were used as the samples. Results are shown in Table 2.

As is evident from Table 2, the rates of promoting the lipolysis in Experimental Examples 10 to 13 greatly exceeded values obtained by adding the rates of promoting the lipolysis of the respective ingredients that composed each Experimental Example in the single preparation (see Table 1-1). On the contrary, the rates of promoting the lipolysis in Comparative Experimental Examples 5 to 7 were below the value obtained by adding the rates of promoting the lipolysis of the respective ingredients that composed each Experimental Example in the single preparation (see Table 1-1).

These results indicate that the component (B) that is the combination of two or more substances in the composition of the present invention also exerts the synergistic effect of the component (A) and the component (B) and exerts the unexpectedly prominent effect of promoting the lipolysis in the same manner as when the component (B) is the single substance.

TABLE 2

Rate of promoting lipolysis

| | Combination of respective ingredients | |
|---|---|---|
| Experimental Example 10 | Lactoferrin 10 ppm + *Coleus forskohlii* extract 10 ppm + *Durvillaea* extract 10 ppm | 155 |
| Experimental Example 11 | Lactoferrin 10 ppm + *Coleus forskohlii* extract 10 ppm + Rosemary extract 10 ppm | 205 |
| Experimental Example 12 | Lactoferrin 10 ppm + *Durvillaea* extract 10 ppm + Rosemary extract 10 ppm | 89 |
| Experimental Example 13 | Lactoferrin 10 ppm + *Coleus forskohlii* extract 10 ppm + *Durvillaea* extract 10 ppm + Rosemary extract 10 ppm | 312 |
| Comparative Experimental Example 5 | Pine bark extract (*Pinus radiata*) 10 ppm + *Coleus forskohlii* extract 10 ppm | 36 |

TABLE 2-continued

Rate of promoting lipolysis

| | Combination of respective ingredients | |
|---|---|---|
| Comparative Experimental Example 6 | Pine bark extract (*Pinus radiata*) 10 ppm + *Durvillaea* extract 10 ppm | 1 |
| Comparative Experimental Example 7 | Pine bark extract (*Pinus radiata*) 10 ppm + Rosemary extract 10 ppm | 16 |

The invention claimed is:

1. A composition for oral administration, comprising:
   (A) lactoferrin; and
   (B) at least one ingredient selected from the group consisting of a *Durvillaea* extract, raspberry ketone, an artichoke leaf extract, a rosemary extract, a *Coleus forskohlii* extract, and an extract from a cacao seed,
   wherein the lactoferrin and the at least one ingredient (B) are combined at a ratio of from 10:1 to 1:10 as an intake per day.

2. The composition of claim 1,
   wherein the composition is a food product, a feedstuff, or a pharmaceutical product.

3. The composition of claim 1, comprising the extract of a cacao seed.

4. The composition of claim 1, comprising the extract of a cacao seed, wherein the cacao extract is an extract obtained by a process comprising extracting a cacao with alcohol.

5. A composition for oral administration, comprising:
   (A) lactoferrin; and
   (B) at least one ingredient selected from the group consisting of a *Durvillaea* extract, raspberry ketone, an artichoke leaf extract, a rosemary extract, isoflavone, a *Coleus forskohlii* extract, and an extract from a cacao seed,
   wherein the lactoferrin and the at least one ingredient (B) are combined at a ratio of from 10:1 to 1:10 as an intake per day, and wherein composition comprises the extract of a cacao seed.

6. A composition for oral administration, comprising:
   (A) lactoferrin; and
   (B) at least one ingredient selected from the group consisting of a *Durvillaea* extract, raspberry ketone, an artichoke leaf extract, a rosemary extract, isoflavone, a *Coleus forskohlii* extract, and an extract from a cacao seed,
   wherein the lactoferrin and the at least one ingredient (B) are combined at a ratio of from 10:1 to 1:10 as an intake per day, wherein the composition comprises the extract of a cacao seed, and wherein the cacao extract is an extract obtained by a process comprising extracting a cacao with alcohol.

7. A method of giving an effect of promoting lipolysis to a food product or a feedstuff, the method comprising:
   adding the composition of claim 1 to a food product or a feedstuff.

8. The method of claim 7,
   wherein the composition comprises the lactoferrin in an amount of from 5 mg/day to 5,000 mg/day as an intake per day for human.

9. The method of claim 8,
   wherein the composition comprises the lactoferrin in an amount of from 100 mg/day to 5,000 mg/day as the intake per day for human.

10. The method of claim 7,
    wherein the composition comprises the at least one ingredient in an amount of from 0.01 mg/day to 50 g/day as an intake per day for human.

11. The method of claim 10,
    wherein the composition comprises the at least one ingredient in an amount of from 1 mg/day to 1000 mg/day as the intake per day for human.

12. The method of claim 7,
    wherein the lactoferrin and the at least one ingredient are combined in a ratio of from 3:1 to 1:3 as the intake per day.

13. A method for promoting lipolysis, the method comprising:
    administering the composition of claim 1 to a subject in need thereof.

14. The method of claim 13,
    wherein the composition is orally administered.

15. The method of claim 14,
    wherein the composition is a food product, a feedstuff, or a pharmaceutical product.

16. The method of claim 13,
    wherein the composition comprises the lactoferrin in an amount of from 5 mg/day to 5,000 mg/day as an intake per day for human.

17. The method of claim 16,
    wherein the composition comprises the lactoferrin in an amount of from 100 mg/day to 5,000 mg/day as the intake per day for human.

18. The method of claim 13,
    wherein the composition comprises the at least one ingredient in an amount of from 0.01 mg/day to 50 g/day as an intake per day for human.

19. The method of claim 18,
    wherein the composition comprises the at least one ingredient in an amount of from 1 mg/day to 1000 mg/day as the intake per day for human.

20. The method of claim 13,
    wherein the lactoferrin and the at least one ingredient are combined in a ratio of from 3:1 to 1:3 as the intake per day.

* * * * *